US012648729B2

(12) United States Patent (10) Patent No.: US 12,648,729 B2
Odan et al. (45) Date of Patent: Jun. 9, 2026

(54) MEASUREMENT APPARATUS, MEASUREMENT METHOD, AND NON-TRANSITORY STORAGE MEDIUM

(71) Applicant: JVCKENWOOD Corporation, Yokohama (JP)

(72) Inventors: Shohei Odan, Yokohama (JP); Takayuki Sugahara, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 439 days.

(21) Appl. No.: 18/171,460

(22) Filed: Feb. 20, 2023

(65) Prior Publication Data

US 2023/0200714 A1 Jun. 29, 2023

Related U.S. Application Data

(63) Continuation of application No. PCT/JP2021/023897, filed on Jun. 24, 2021.

(30) Foreign Application Priority Data

Aug. 28, 2020 (JP) ................................. 2020-145070

(51) Int. Cl.
*A61B 5/00* (2006.01)
*A61B 5/0205* (2006.01)
(52) U.S. Cl.
CPC .......... *A61B 5/4035* (2013.01); *A61B 5/0205* (2013.01)
(58) Field of Classification Search
None
See application file for complete search history.

(56) References Cited

U.S. PATENT DOCUMENTS

2005/0240087 A1* 10/2005 Keenan .................. A61B 5/318
600/509
2009/0198147 A1 8/2009 Ono et al.
(Continued)

FOREIGN PATENT DOCUMENTS

JP 2009-178456 8/2009
JP 5327458 10/2013

OTHER PUBLICATIONS

Fred Shaffer et al. An Overview of Heart Rate Variability Metrics and Norms. Front Public Health. Sep. 28, 2017;5:258. doi: 10.3389/fpubh.2017.00258. PMID: 29034226; PMCID: PMC5624990. viewed on May 3, 2025 (Year: 2017).*

(Continued)

*Primary Examiner* — Unsu Jung
*Assistant Examiner* — James Moss
(74) *Attorney, Agent, or Firm* — Amin, Turocy & Watson, LLP

(57) ABSTRACT

A measurement apparatus includes a first biometric sensor configured to measure, as a biological signal, at least one of a brain wave signal and a pulse wave signal of a living body, a second biometric sensor configured to measure a respiratory rate of the living body per unit time, a differential operation unit configured to calculate a differential value of a periodic feature of the biological signal, an activity level analysis unit configured to analyze an activity level of an autonomic nerve of the living body based on the differential value, and an activity level correction unit configured to correct the activity level of the autonomic nerve by eliminating a component caused by respiration of the living body and included in the activity level of the autonomic nerve based on the respiratory rate of the living body per unit time.

5 Claims, 11 Drawing Sheets

(56) References Cited

U.S. PATENT DOCUMENTS

| | | | |
|---|---|---|---|
| 2010/0228139 A1* | 9/2010 | Nanba ................. | A61B 5/4035 |
| | | | 600/509 |
| 2017/0095670 A1* | 4/2017 | Ghaffari ............... | A61M 21/02 |
| 2017/0231490 A1* | 8/2017 | Toth ...................... | G16H 40/63 |
| | | | 600/558 |

OTHER PUBLICATIONS

Alberto Hernando et al., "Inclusion of Respiratory Frequency Information in Heart Rate Variability Analysis for Stress Assessment," in IEEE Journal of Biomedical and Health Informatics, vol. 20, No. 4, pp. 1016-1025, Jul. 2016, doi: 10.1109/JBHI.2016.2553578 viewed on May 7, 2025 (Year: 2016).*
Raquel Bailon et al., "Analysis of Heart Rate Variability Using Time-Varying Frequency Bands Based on Respiratory Frequency," 2007 29th Annual International Conference of the IEEE Engineering in Medicine and Biology Society, Lyon, France, 2007, pp. 6674-6677, doi: 10.1109/IEMBS.2007.4353891 (Year: 2006).*
International Search Report and Written Opinion for International Application No. PCT/JP2021/023897 mailed on Aug. 10, 2021, 8 pages.
Extended European Search Report for European Patent Application No. 21860947.7 dated Dec. 7, 2023.
European Office Action for European Patent Application No. 21860947.7 dated Aug. 4, 2025.
Badra, et al. "Respiratory modulation of human autonomic rhythms", Am J Physiol Hear Circ Physiol 280: H2674-H2688, 2001.
Yasuma, et al. "Respiratory sinus arrhythmia: why does the heartbeat synchronize with respiratory rhythm?", Chest Journal Feb. 2004.

* cited by examiner

CONTROLLER — 20

FIRST BIOMETRIC SENSOR — 11

NOSE SENSOR — 12B

OPERATION UNIT — 13

COMMUNICATION UNIT — 14

BIOLOGICAL INFORMATION ACQUISITION UNIT — 21

DIFFERENTIAL OPERATION UNIT — 22

ACTIVITY LEVEL ANALYSIS UNIT — 23

ACTIVITY LEVEL CORRECTION UNIT — 24

ACTIVITY LEVEL OUTPUT UNIT — 25

COMMUNICATION CONTROLLER — 26

10B

12B    U

1

MEASUREMENT APPARATUS, MEASUREMENT METHOD, AND NON-TRANSITORY STORAGE MEDIUM

CROSS-REFERENCE TO RELATED APPLICATIONS

This application is a Continuation of PCT International Application No. PCT/JP2021/023897 filed on Jun. 24, 2021 which claims the benefit of priority from Japanese Patent Application No. 2020-145070 filed on Aug. 28, 2020, the entire contents of both of which are incorporated herein by reference.

FIELD OF THE INVENTION

The present application relates to a measurement apparatus, a measurement method, and a program.

BACKGROUND OF THE INVENTION

A technology for measuring a state of activity of autonomic nervous system of a living body is known. For example, Japanese Laid-open Patent Publication No. 2009-178456 A discloses a technology of giving electrical stimulation to a living body and measuring activity of autonomic nervous system based on a comparison result between a pulse wave signal before the electrical stimulation is given and a pulse wave signal after the electrical stimulation is given.

It is known that a change of internal pressure of a chest cavity due to respiratory movement affects a measurement result of a pulse wave and thereby the measurement result of the pulse wave may include an error. Various efforts are made such that a pulse wave and a brain wave are measured while respiration of a target person is adjusted to a predetermined condition. However, a measurement apparatus therefor is expensive and, in some cases, it takes time and efforts for the measurement.

A measurement apparatus, a measurement method, and a non-transitory storage medium is disclosed

SUMMARY OF THE INVENTION

According to one aspect of the present application, there is provided a measurement apparatus comprising: a first biometric sensor configured to measure, as a biological signal, at least one of a brain wave signal and a pulse wave signal of a living body; a second biometric sensor configured to measures a respiratory rate of the living body per unit time; a differential operation unit configured to calculate a differential value of a periodic feature of the biological signal; an activity level analysis unit configured to analyzes an activity level of an autonomic nerve of the living body based on the differential value of the periodic feature of the biological signal; and an activity level correction unit configured to correct the activity level of the autonomic nerve of the living body by eliminating a component that is caused by respiration of the living body and that is included in the activity level of the autonomic nerve of the living body, based on the respiratory rate of the living body per unit time.

According to one aspect of the present application, there is provided a measurement method comprising: measuring, as a biological signal, at least one of a brain wave signal and a pulse wave signal of a living body; measuring a respiratory rate of the living body per unit time; calculating a differential value of a periodic feature of the biological signal; analyzing an activity level of an autonomic nerve of the living body based on the differential value of the periodic feature of the biological signal; and correcting the activity level of the autonomic nerve of the living body by eliminating a component that is caused by respiration of the living body and that is included in the activity level of the autonomic nerve of the living body based on the respiratory rate of the living body per unit time.

According to one aspect of the present application, there is provided a non-transitory storage medium that stores a program that causes a computer to execute: measuring, as a biological signal, at least one of a brain wave signal and a pulse wave signal of a living body; measuring a respiratory rate of the living body per unit time; calculating a differential value of a periodic feature of the biological signal; analyzing an activity level of an autonomic nerve of the living body based on the differential value of the periodic feature of the biological signal; and correcting the activity level of the autonomic nerve of the living body by eliminating a component that is caused by respiration of the living body and that is included in the activity level of the autonomic nerve of the living body based on the respiratory rate of the living body per unit time.

The above and other objects, features, advantages and technical and industrial significance of this application will be better understood by reading the following detailed description of presently preferred embodiments of the application, when considered in connection with the accompanying drawings.

DETAILED DESCRIPTION OF THE INVENTION

Embodiments according to the present application will be described in detail below with reference to accompanying drawings. The present application is not limited by the embodiments below, and includes configurations that are achieved by combining the embodiments when multiple embodiments are provided. Furthermore, in the embodiments below, the same components are denoted by the same reference symbols, and repeated explanation will be omitted.

Overview

Figure 1:
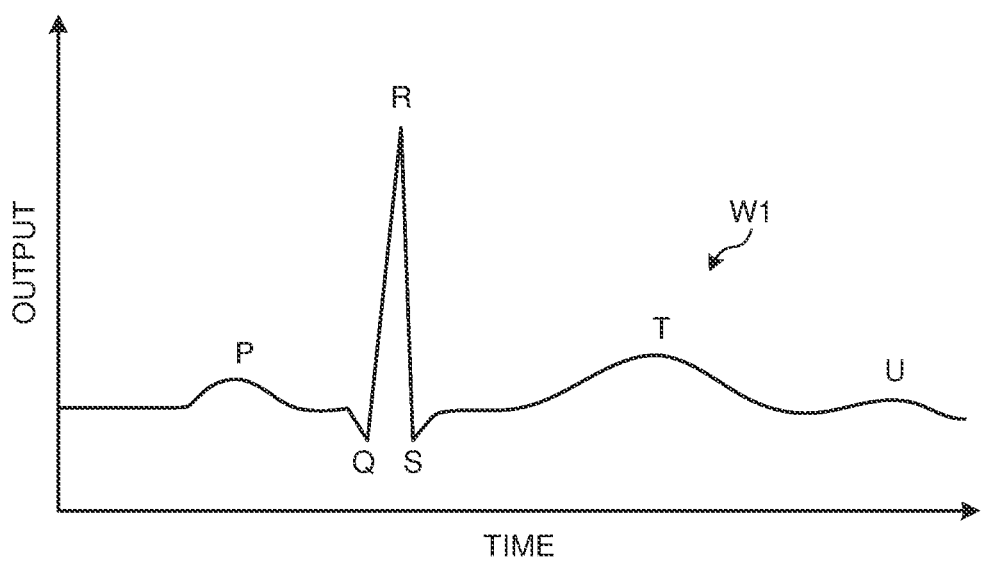
FIG. 1 is a diagram for explaining a physiological feature of a biological signal.
Figure 2:
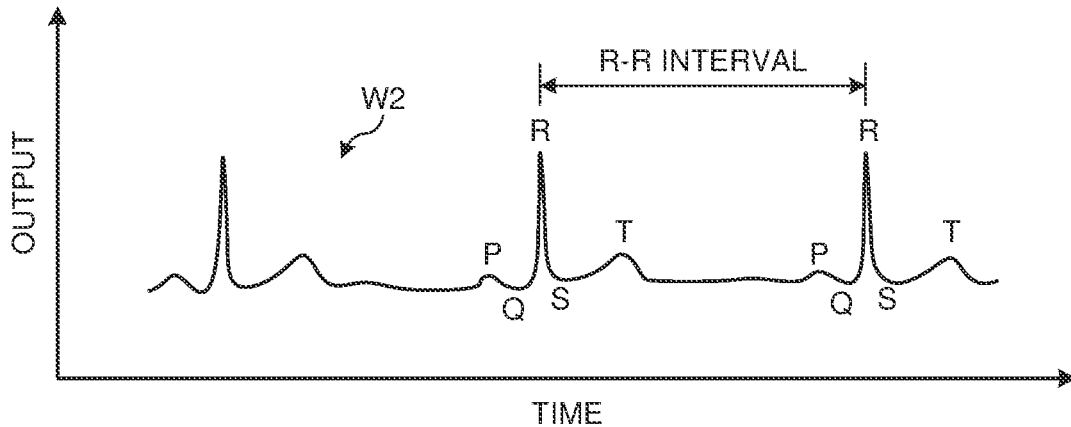
FIG. 2 is a diagram for explaining the physiological feature of the biological signal.

To explain the embodiments, a physiological feature of a biological signal of a living body measured in the embodiments will be described. FIG. 1 and FIG. 2 are diagrams for explaining the physiological feature of the biological signal. Explanation will be given based on the assumption that the biological signals illustrated in FIG. 1 and FIG. 2 are pulse wave signals related to a pulse wave, but the present application is not limited to this example. For example, the biological signal may be an electroencephalogram related to a brain wave.

A pulse beat of a living tissue occurs due to automatic firing of pacemaker cells in a sinus node of a heart. Rhythm of the pulse beat is largely affected by both of a sympathetic nerve and a parasympathetic nerve. The sympathetic nerve acts to accelerate a cardiac activity. The parasympathetic nerve acts to suppress a cardiac activity. In a normal state, the sympathetic nerve and the parasympathetic nerve act in an antagonistic manner. In a rest state or a state close to the rest state, the parasympathetic nerve acts in a dominant manner.

As illustrated in FIG. 1, a waveform W1 that represents an electrocardiogram includes a P wave, a QRS wave, a T wave, and a U wave. As for a heart rate variability, a detection of an R wave that is a vertex of the QRS wave is measured as a single pulse beat. As illustrated in FIG. 2, in a waveform W2 that represents an electrocardiogram, variation of an interval between R waves in an electrocardiogram, that is, fluctuation of a duration of an R-R interval that represents the interval between the R waves, is used as an autonomic nerve index that represents information on an autonomic nerve. The fluctuation of the duration of the R-R interval is increased in a resting state and decreased in a stress state. In the present embodiment, the information on the autonomic nerve may be referred to as an activity level of the autonomic nerve.

The fluctuation of the duration of the R-R interval includes some kinds of characteristic fluctuation. One kind of the fluctuation is fluctuation of a low-frequency component that appears at around 0.1 Hz. The fluctuation of the low-frequency component is caused by variation of activity of a sympathetic nervous system due to a feedback regulation of a blood pressure of a blood vessel. Another kind of fluctuation is fluctuation of a high-frequency component that reflects variation that is synchronized with respiration, that is, respiratory sinus arrhythmia. The fluctuation of the high-frequency component is caused by direct interference of a respiratory center to an anterior vagus nerve, pulmonary stretch receptors, and baroreceptor reflex due to a change in blood pressure caused by respiration. The fluctuation of the high-frequency component is used as a parasympathetic nerve index that indicates a degree of activity of the parasympathetic nerve that affects the heart. That is, among waveform components that are obtained by measuring fluctuation of an R-R wave interval of the electrocardiogram, a power spectrum of the low-frequency component represents a degree of activity of the sympathetic nerve and a power spectrum of the high-frequency component represents a degree of activity of the parasympathetic nerve.

In the present embodiment, when a degree of activity of an autonomic nerve of a target person is to be calculated, a certain tendency is corrected based on the physiological knowledge, where the tendency is that if a respiratory rate is reduced while a parasympathetic nerve is in an active state, a low-frequency component increases since an influencing component caused by respiration is reflected near a low-frequency band.

First Embodiment

Figure 3:
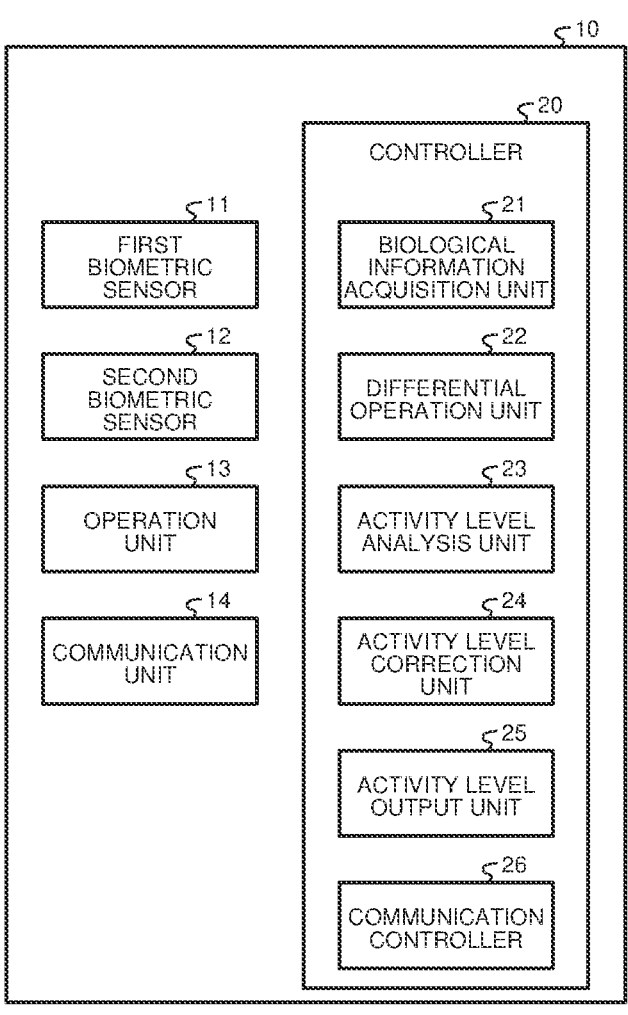
FIG. 3 is a block diagram illustrating a configuration example of a measurement apparatus according to a first embodiment.

A configuration of a measurement apparatus according to a first embodiment will be described below with reference to FIG. 3. FIG. 3 is a block diagram illustrating a configuration example of the measurement apparatus according to the first embodiment.

As illustrated in FIG. 3, a measurement apparatus 10 includes a first biometric sensor 11, a second biometric sensor 12, an operation unit 13, a communication unit 14, and a controller 20. The measurement apparatus 10 is a wearable device that is worn on a body of a user, for example. The wearable device may be a smart watch as an example, but not limited thereto.

The first biometric sensor 11 measures first biological information on a target person. The first biometric sensor 11 measures, for example, a pulse wave of the target person as the first biological information which is available instead of electrocardiogram by regarding an interval between peaks of adjacent second-order differential pulse waves as the R-R interval. The first biometric sensor 11 may be implemented by, for example, a transmission-type photoelectric pulse sensor that includes a light-emitting unit for emitting light and a light-receiving unit for receiving the light. In this case, the first biometric sensor 11 is configured to sandwich a fingertip between the light-emitting unit and the light-receiving unit, cause the light-receiving unit to receive the light emitted from the light-emitting unit through the fingertip, and measure a pulse wave of the target person, for example. Specifically, a blood flow increases with an increase in a pulse wave pressure of the target person, and the blood flow decreases with a decrease in the pulse wave pressure. The first biometric sensor 11 measures the pulse wave of the target person by, for example, detecting a change in transmittance of the light due to a change in the blood flow. The first biometric sensor 11 detects, for example, the pulse wave of the target person that changes from moment to moment, and converts a detection result of the pulse wave to a digital signal by using an analog-to-digital (A/D) converter (not illustrated). The first biometric sensor 11 outputs the digital signal of the pulse wave to the controller 20. The first biometric sensor 11 is not limited to the transmission-type photoelectric pulse sensor, and is not specifically limited as long as the sensor is able to measure an electrocardiogram or a pulse wave.

The second biometric sensor 12 measures second biological information on the target person. The second biometric sensor 12 measures, for example, a respiratory status of the target person as the second biological information. The second biometric sensor 12 determines whether respiration of the target person is expiration or inspiration, for example. The second biometric sensor 12 measures a respiratory rate of the target person per unit time. The second biometric sensor 12 may be implemented by a respiration sensor.

The second biometric sensor 12 is not specifically limited as long as it is possible to detect air that enters and exits a mouth or a nose of the target person. The second biometric sensor 12 may be a sensor that indirectly detects the respiratory status of the target person. As a method of indirectly detecting the respiratory status of the target person, for example, it may be possible to adopt a method of detecting a change of a perimeter length of a trunk (for example, a chest or an abdomen) caused by respiration. In this case, the second biometric sensor 12 may be configured using a stretchable variable resistance element in which an electrical resistance value changes due to stretch, for example. The second biometric sensor 12 may perform determination on an expiration period or an inspiration period by measuring a change of the perimeter length of the trunk of the target person by using the stretchable variable resistance element, for example. The second biometric sensor 12 may measure the respiratory rate by measuring the number of changes of the perimeter length of the trunk of the target person by using the stretchable variable resistance element, for example.

The operation unit 13 receives various kinds of operation on the measurement apparatus 10. The operation unit 13 receives, for example, operation of starting measurement of an activity level of an autonomic nerve of the target person and operation of terminating the measurement of the activity level of the autonomic nerve of the target person. The operation unit 13 may be implemented by, for example, a touch panel, buttons, switches, or the like.

The communication unit 14 transmits and receives information between the measurement apparatus 10 and an external apparatus. The communication unit 14 transmits and receives information between, for example, the measurement apparatus 10 and an external server apparatus. The communication unit 14 transmits and receives information between, for example, the measurement apparatus 10 and a terminal device, such as a smartphone, that is owned by the target person. The communication unit 14 may be implemented by a communication unit, such as Bluetooth (registered trademark) or Wi-Fi (registered trademark), for example.

The controller 20 controls the units of the measurement apparatus 10 respectively. The controller 20 is implemented by, for example, causing a central processing unit (CPU), a micro processing unit (MPU), or the like to execute a program (for example, the program according to the present application) that is stored in a storage (not illustrated) by using a random access memory (RAM) or the like as a work area. The controller 20 may be implemented by, for example, an integrated circuit, such as an application specific integrated circuit (ASIC) or a field programmable gate array (FPGA). The controller 20 may be implemented by a combination of software and a hardware circuit.

The controller 20 includes a biological information acquisition unit 21, a differential operation unit 22, an activity level analysis unit 23, an activity level correction unit 24, an activity level output unit 25, and a communication controller 26.

The biological information acquisition unit 21 acquires the first biological information from the first biometric sensor 11. Specifically, the biological information acquisition unit 21 acquires the information on the pulse wave of the target person from the first biometric sensor 11. The biological information acquisition unit 21 acquires the second biological information from the second biometric sensor 12. Specifically, the biological information acquisition unit 21 acquires the information on the respiratory status of the target person from the second biometric sensor 12.

The differential operation unit 22 identifies times at which R waves are detected based on the first biological information. The differential operation unit 22 calculates an R-R interval of the pulse wave which indicates a time interval between a certain R wave and an adjacent R wave based on the times at which the R waves are detected. The differential operation unit 22 calculates fluctuation (differential value) between certain piece of R-R interval data and an adjacent piece of R-R interval data. The differential operation unit 22 outputs the calculated differential value of R-R interval values of the pulse wave to the activity level analysis unit 23.

The activity level analysis unit 23 calculates power spectrums of high-frequency components and low-frequency components of the differential value of the R-R interval values of the pulse wave. Specifically, if the differential values of the R-R interval values of the pulse wave does not correspond to chronological data of an equal interval for example, the activity level analysis unit 23 converts the data to chronological data of an equal interval by using cubic spline interpolation or the like. The activity level analysis unit 23 performs orthogonal transformation on the differential values of the R-R interval values by the fast Fourier transform or the like. That is, the activity level analysis unit 23 converts the chronological data to data related to a frequency. Here, to ensure a satisfactory sampling value, it is preferable to use a frequency band of around 0.1 Hz when the power spectrums of the low-frequency components are obtained. In this case, in general, it is preferable to ensure data of about 30 seconds to 60 seconds.

The activity level analysis unit 23 calculates the power spectrums of the high-frequency components and the low-frequency components of the differential values of the R-R interval values of the pulse wave subjected to the orthogonal transformation by the fast Fourier transform or the like. The activity level analysis unit 23 outputs a total sum of the power spectrums of the high-frequency components as RRHF. The activity level analysis unit 23 outputs a total sum of the power spectrums of the low-frequency components as RRLF.

The activity level analysis unit 23 calculates an activity level of an autonomic nerve based on the total sum of the power spectrums of the high-frequency components and the total sum of the power spectrums of the low-frequency components. For example, AN(BV) is represented by Expression (1) below, where AN(BV) represents the activity level of the autonomic nerve at a respiratory rate BV, RRHF(BV) represents the total sum of the power spectrums of the high-frequency components, and RRLF(BV) represents the total sum of the power spectrums of the low-frequency components. Meanwhile, the respiratory rate BV represents an actual respiratory rate.

$$AN(BV) = \frac{RRLF(BV)}{RRHF(BV)} \qquad (1)$$

The activity level correction unit 24 corrects the activity level of the autonomic nerve that is calculated by the activity level analysis unit 23 using Expression (1). Specifically, the activity level correction unit 24 corrects the activity level of the autonomic nerve based on the respiratory status of the target person.

An influence of the respiratory status on the activity level of the autonomic nerve will be described below. The respiratory center is present in a brain stem and forms a periodic rhythm between inspiration and expiration. The respiratory center receives input from chemoreceptors in the center and peripheral, and adjusts frequency of impulse in accordance with an amount of oxygen needed for a living body. Further, the respiratory center receives signals from a large number of sites, such as pulmonary stretch receptors, muscle spindles of respiration muscles or other muscles, tendons, and joints, and is also cortically dominated by higher-level sites. Therefore, it is known that respiration has both of autonomy and voluntary. With regard to the autonomy, in the physiological psychology, respiration may change mainly due to stress and an emotional change.

In general, when the sympathetic nerve is activated, the respiratory rate is regular and accelerated, and, when the parasympathetic nerve is activated, the respiratory rate slows down. It is preferable to eliminate the situation as described above as much as possible since the situation is largely linked with the autonomic nerves. Thus the activity level correction unit 24 corrects the activity level of the autonomic nerve based on the respiratory status of the target person measured by the second biometric sensor 12. The respiratory status of the target person may include information on an expiration period, an inspiration period, the respiratory rate, and a reference clock. The respiratory rate is measured as a respiratory rate per unit time, and therefore, a timing of a change from "inspiration to expiration" or a change from "expiration to inspiration" is measured as a single count. The number of counted timings of the change from "inspiration to expiration" or the change from "expiration to inspiration" in a period between a current time and a past predetermined time (for example, past one minute) is used as the respiratory rate BV. Specifically, with use of what is called a sliding window in which a window of a fixed time interval is slid, the number of counts that are measured during the time interval of the window is used as the respiratory rate BV.

The activity level correction unit 24 corrects the activity level of the autonomic nerve represented by Expression (1) in a manner as described below. It is said that the respiratory rate in a normal steady state is 12 to 20 per minutes. Therefore, in the present embodiment, it is assumed that the respiratory rate is corrected to 15 per minutes, which is an approximately intermediate value. Here, assuming that a regression coefficient of a logarithm of the respiratory rate BV is represented by a, a correction formula may be represented by Expression (2) below. 15 in Expression (2) represents the respiratory rate per minute (a measurement period of the respiratory rate BV) in the steady state, but is not limited to 15, and any value (not limited to an integer) in a range from 12 to 20 is applicable. Further, it may be possible to use the respiratory rate of the target person per minute in the steady state, and, in this case, it may be possible to use a value that exceeds the range from 12 to 20.

$$\log(AN(15)) - \log(AN(BV)) = a(\log(15) - \log(BV)) \qquad (2)$$

Expression (2) may be organized as represented by Expression (3) below.

$$AN(BV) = \frac{RRLF(BV)}{RRHF(BV)(15/BV)^{\alpha}} \qquad (3)$$

In Expression (3), $(15/BV)^{\alpha}$ represents a correction term. The activity level correction unit 24 is able to eliminate most of influence of respiration by using Expression (3). The activity level correction unit 24 outputs information on the activity level of the autonomic nerve corrected by Expression (3) to the activity level output unit 25.

Meanwhile, the regression coefficient $\alpha$ may be obtained by acquiring data of a predetermined number of persons in different groups, such as different ages, different genders, or different biological characteristics. The regression coefficient $\alpha$ may be stored in a storage (not illustrated). The activity level correction unit 24 is able to correct the activity level of the autonomic nerve with high accuracy by using the regression coefficient $\alpha$ that is stored in the storage (not illustrated).

For example, to obtain the regression coefficient $\alpha$, about 20 subjects are grouped based on biological information, such as age or vital capacity, as a variable in a prediction formula. It is possible to obtain the regression coefficient $\alpha$ by preparing multiple parameters as variables in the prediction formula and performing regression analysis. For example, it is possible to obtain the regression coefficient $\alpha$ by grouping the 20 subjects into four groups each including five subjects based on conditions and performing regression analysis. Meanwhile, depending on the parameter of each of the subjects, the four divided groups do not always equally include five subjects. For example, depending on the parameter of each of the subjects, groups including four subjects, six subjects, seven subjects, and three subjects may be obtained.

For example, if calculation is performed by assuming that the respiratory rate per minute in the steady state is 15, $\alpha = 1.8$. This is a value obtained from experiments performed on the subjects. The respiratory rate need not always obtained per minute, but may be obtained in a different unit of time. It is preferable that $\alpha$ is about 1.8, but $\alpha$ is not limited thereto. For example, it may be possible to set a range of a such that $1.1 \le \alpha \le 2.5$. This range is an example in which the regression coefficient is calculated by changing each of the parameters by about $\pm 10\%$ while taking into account variation due to environments or a measurement error.

A magnitude of the activity level of the autonomic nerve represented by Expression (3) changes depending on magnitudes of the respiratory rate BV and the regression coefficient $\alpha$. Specifically, the activity level of the autonomic nerve is corrected so as to decrease with an increase in the correction term. For example, when the range of $\alpha$ is set such that $1.1 \le \alpha \le 2.5$, the correction term is equal to or larger than 1 if the respiratory rate BV is equal to or smaller than 15, and the correction term is smaller than 1 if the respiratory rate BV is larger than 15. That is, the activity level of the autonomic nerve is calculated so as to be reduced as compared to the non-corrected autonomic nerve activity level if the respiratory rate BV is equal to or smaller than 15, and the activity level of the autonomic nerve is calculated so as to be increased as compared to the non-corrected autonomic nerve activity level if the respiratory rate BV is larger than 15.

The activity level output unit 25 outputs information, such as a value indicating the activity level of the autonomic nerve or a graph represented by a specific duration, by using a predetermined man-machine interface, such as an external display apparatus.

The communication controller 26 controls the communication unit 14 and controls communication between the measurement apparatus 10 and an external apparatus. The communication controller 26 controls the communication unit 14 and controls communication between the measurement apparatus 10 and an external computer, for example.

Meanwhile, if the measured respiratory rate is a respiratory rate in the steady state, the activity level correction unit 24 corrects the activity level of the autonomic nerve in accordance with the measured respiratory rate. For example, if the measurement result of the respiratory rate of the target person obtained by the second biometric sensor 12 is equal to or smaller than 11 or equal to or larger than 21, the activity level correction unit 24 may determine that the state of the measured respiratory rate is an unsteady state. In this case, the activity level correction unit 24 may discard the calculation result of the activity level of the autonomic nerve obtained by the activity level analysis unit 23, for example. Further, the activity level correction unit 24 may display an alarm indicating "measurement is impossible" on an external display apparatus or the like, for example. Meanwhile, the range of the respiratory rate in which the state thereof is determined as an unsteady state is not limited to a range equal to or smaller than 11 and equal to or larger than 21, but may be determined based on the respiratory rate of the target person in the steady state.

Furthermore, a respiration influencing factor includes a heart rate difference that may occur between inspiration and expiration in single respiration due to respiratory sinus arrhythmia. The heart rate difference may cause an error when the activity index of the parasympathetic nerve is calculated. In the present embodiment, by performing analysis while separating a peak of the R wave in expiration and a peak of the R wave in inspiration, it is possible to eliminate the influencing factor due to respiratory sinus arrhythmia.

Figure 4:
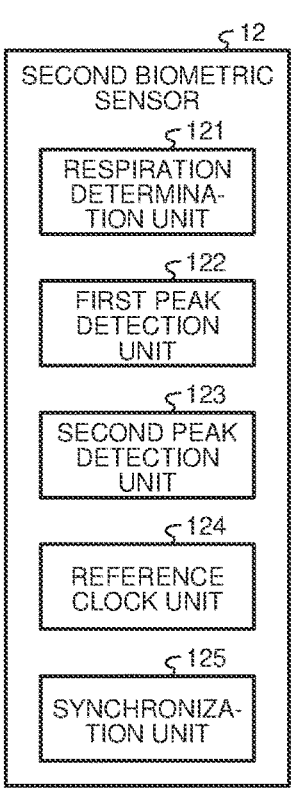
FIG. 4 is a block diagram illustrating a configuration example of a second biometric sensor according to the first embodiment.

A configuration of the second biometric sensor that is able to perform measurement while separating the peak of the R wave in expiration and the peak of the R wave in inspiration will be described below with reference to FIG. 4. FIG. 4 is a block diagram illustrating a configuration example of the second biometric sensor according to the first embodiment.

As illustrated in FIG. 4, the second biometric sensor 12 includes a respiration determination unit 121, a first peak detection unit 122, a second peak detection unit 123, a reference clock unit 124, and a synchronization unit 125.

The respiration determination unit 121 determines whether the respiration of the target person is expiration or inspiration. The respiration determination unit 121 determines whether the respiration is expiration or inspiration in accordance with a direction of a flow of air around a mouth or a nose, for example. The respiration determination unit 121 determines that the respiration is inspiration if the direction of the flow of the air around the mouth or the nose is a direction toward the target person. The respiration determination unit 121 determines that the respiration is expiration if the direction of the flow of the air around the mouth or the nose is a direction away from the target person.

Figure 5:
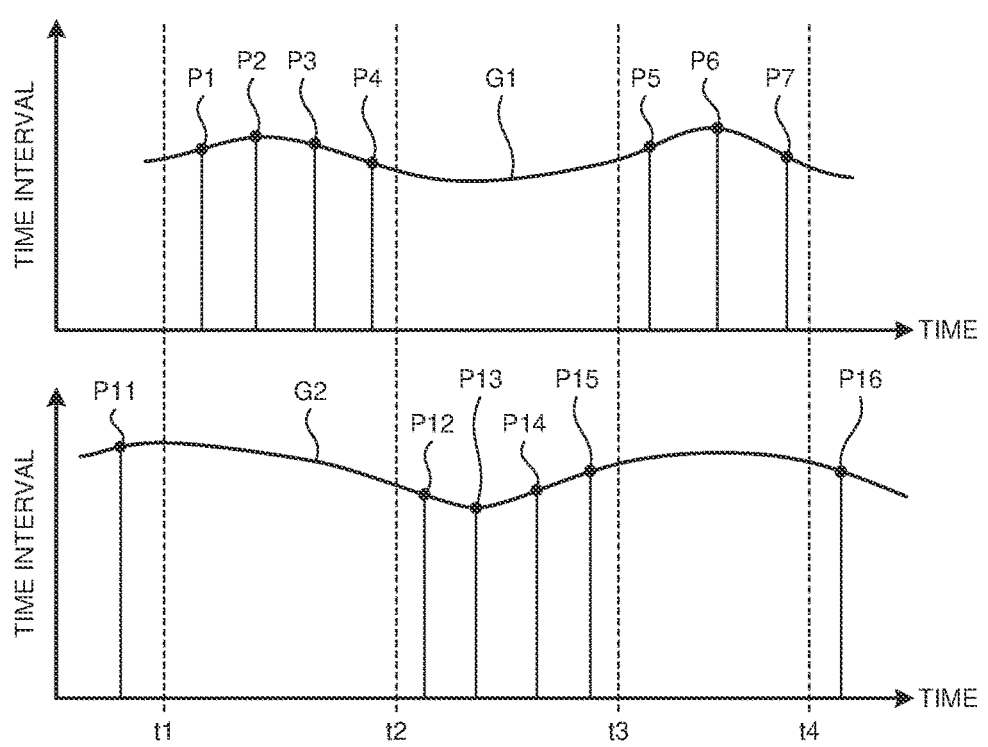
FIG. 5 is a diagram for explaining variation in a duration of an R-R interval.

The first peak detection unit 122 detects a peak of the R wave in an inspiration period. The second peak detection unit 123 detects a peak of the R wave in an expiration period. FIG. 5 is a diagram for explaining fluctuation of the duration of the R-R interval. FIG. 5 illustrates a graph G1 and a graph G2. The graph G1 is a graph that represents fluctuation of the duration of the R-R interval in the inspiration period. The graph G2 is a graph that represents fluctuation of the duration of the R-R interval in the expiration period. In the graph G1 and the graph G2, the vertical axis represents a time interval between an R wave and a next R wave, and the horizontal axis represents a reference clock.

In FIG. 5, time intervals from a time t1 to a time t2, from the time t2 to a time t3, and from the time t3 to a time t4 are the same. In FIG. 5, a period from the time t1 to the time t2 and a period from the time t3 to the time t4 are the inspiration periods, and a period from the time t2 to the time t4 and a period from the time t4 are the expiration periods.

Specifically, the graph G1 is a graph that is obtained by assuming that a first R wave in the inspiration period is adopted as a time of the reference clock and measuring a time interval of a period until a next R wave. In the graph G1, seven measurement points are illustrated. It is indicated that, in the period from the time t1 to the time t2, the measurement is performed at four points, that is, a point P1 to a point P4, and, in the period from the time t3 to the time t4, the measurement is performed at three points, that is, a point P5 to a point P7. That is, the number of times of the measurement may be different even in the same time interval.

The graph G2 is a graph that is obtained by assuming that a first R wave in the expiration period is adopted as a time of the reference clock and measuring a time interval of a period until a next R wave. A point P11 is a measurement point in the expiration period before the time t1. In the graph G2, it is indicated that the measurement is performed at four points, that is, a point P12 to a point P15, in the period from the time t2 to the time t3. A point P16 is a measurement point in the expiration period after the time t4.

In respiration, expiration and inspiration are repeated in a time unit that is about a half of the entire period. Therefore, as indicated by the graph G1 and the graph G2, a period in which data is present during respiration is alternately repeated between expiration and inspiration in a time unit that is about a half.

The reference clock unit 124 outputs a reference clock time to the synchronization unit 125. The synchronization unit 125 generates data in synchronization with a time corresponding to the reference clock on the horizontal axes of the graph G1 and the graph G2 as a first R wave arrival time. The synchronization unit 125 outputs the generated data to the controller 20. The synchronization unit 125 separately outputs the data of the R-R interval in the inspiration period and the data of the R-R interval in the expiration period to the controller 20.

Specifically, the second biometric sensor 12 separately measures fluctuation of the time interval of the R-R wave interval for each of expiration and inspiration as indicated by the graph G1 and the graph G2. The second biometric sensor 12 separately outputs information indicating the fluctuation of the time interval of the R-R wave interval for expiration and information indicating the fluctuation of the time interval of the R-R wave interval for inspiration to the controller 20. That is, the second biometric sensor 12 separately outputs the data of the expiration period and the data of the inspiration period to the controller 20.

The biological information acquisition unit 21 separately acquires the data of the expiration period and the data of the inspiration period from the second biometric sensor 12.

If the data of the expiration period and the data of the inspiration period are not chronological data of an equal interval, The activity level analysis unit 23 separately converts the data to chronological data of an equal interval by using cubic spline interpolation or the like. The activity level analysis unit 23 performs orthogonal transformation 0015 on the data of the expiration period, the data of the inspiration period, and the chronological data thereof by the fast Fourier transform or the like. That is, the activity level analysis unit 23 separately converts the chronological data, the data of the expiration period, and the data of the inspiration period to data related to a frequency. The activity level analysis unit 23 separately calculates an autonomic nerve activity level AN of the expiration period and the inspiration period by using Expression (1) as described above. The activity level analysis unit 23 outputs the autonomic nerve activity level AN of each of the expiration period and the inspiration period to the activity level correction unit 24.

The activity level correction unit 24 corrects the autonomic nerve activity level AN of each of the expiration period and the inspiration period by using Expression (3) as described above. The activity level correction unit 24 outputs the corrected autonomic nerve activity level AN of each of the expiration period and the inspiration period to the activity level output unit 25.

The activity level output unit 25 outputs information, such as a value indicating the autonomic nerve activity level of each of the expiration period and the inspiration period or a graph represented by a specific duration, by using a predetermined man-machine interface, such as an external display apparatus. Further, the activity level output unit 25 may output a value that is obtained by adding the value indicating the activity level of the autonomic nerve of the expiration period and that of the inspiration period and multiplying the sum by ½. In other words, the activity level output unit 25 may output an average value of the activity level of the autonomic nerve of the expiration period and that of the inspiration period. In this manner, by eliminating the respiration influencing factor that occurs depending on the respiratory status from the autonomic nerve activity level that is calculated by using the R-R interval of the electrocardiogram, it is possible to correct the activity level of the autonomic nerve with high accuracy.

Correction Process

Figure 6:
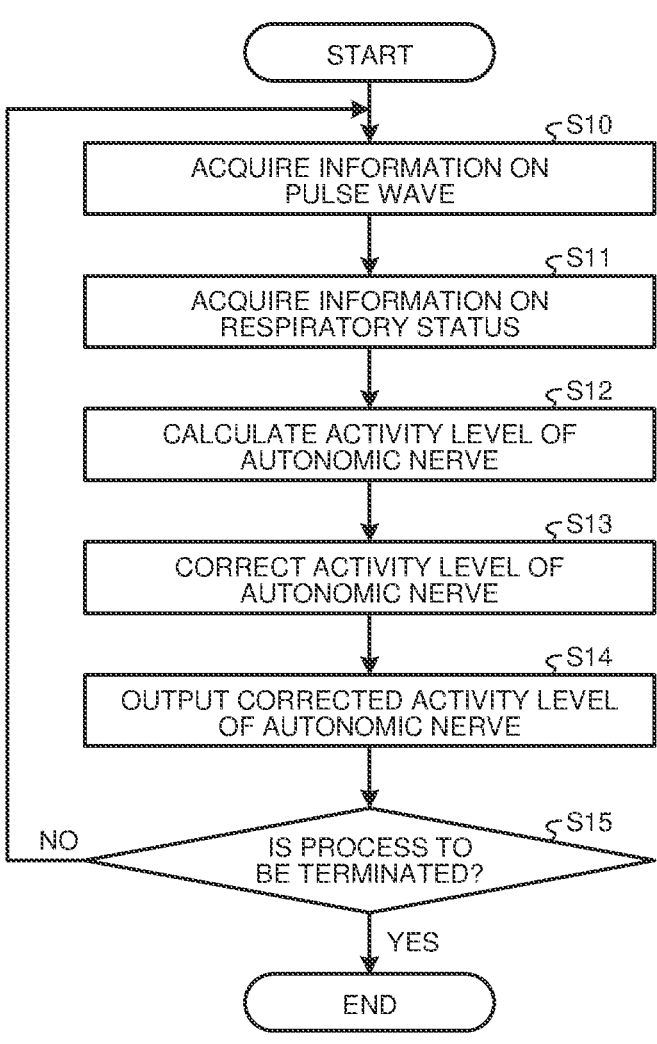
FIG. 6 is a flowchart illustrating an example of a flow of a process for measuring an activity level of an autonomic nerve according to the first embodiment.

Process of measuring the activity level of the autonomic nerve according to the first embodiment will be described below with reference to FIG. 6. FIG. 6 is a flowchart illustrating an example of a flow of the process of measuring the activity level of the autonomic nerve according to the first embodiment.

The biological information acquisition unit 21 acquires information on a pulse wave of a target person from the first biometric sensor 11 (Step S10). The biological information acquisition unit 21 acquires information on a respiratory status of the target person from the second biometric sensor 12 (Step S11).

The activity level analysis unit 23 calculates an activity level of an autonomic nerve of the target person based on the information on the pulse wave of the target person (Step S12). The activity level correction unit 24 corrects the activity level of the autonomic nerve of the target person calculated by the activity level analysis unit 23, based on the information on the respiratory status of the target person (Step S13). The activity level output unit 25 outputs the corrected activity level of the autonomic nerve of the target person (Step S14).

The controller 20 determines whether the process of measuring the activity level of the autonomic nerve of the target person is to be terminated (Step S15). Upon receiving operation of terminating the process of measuring the activity level of the autonomic nerve or operation of turning off a power supply of the measurement apparatus 10 for example, the controller 20 determines that the process of measuring the activity level of the autonomic nerve of the target person is to be terminated. If it is determined that the process of measuring the activity level of the autonomic nerve of the target person is to be terminated (Step S15; Yes), the process in FIG. 6 is terminated. If it is determined that the process of measuring the activity level of the autonomic nerve of the target person is not to be terminated (Step S15; No), the process returns to Step S10.

As described above, in the first embodiment, the activity level of the autonomic nerve is corrected based on the respiratory status of the target person. Therefore, in the first embodiment, it is possible to measure the activity level of the autonomic nerve of the target person with high accuracy.

Second Embodiment

Figure 7:
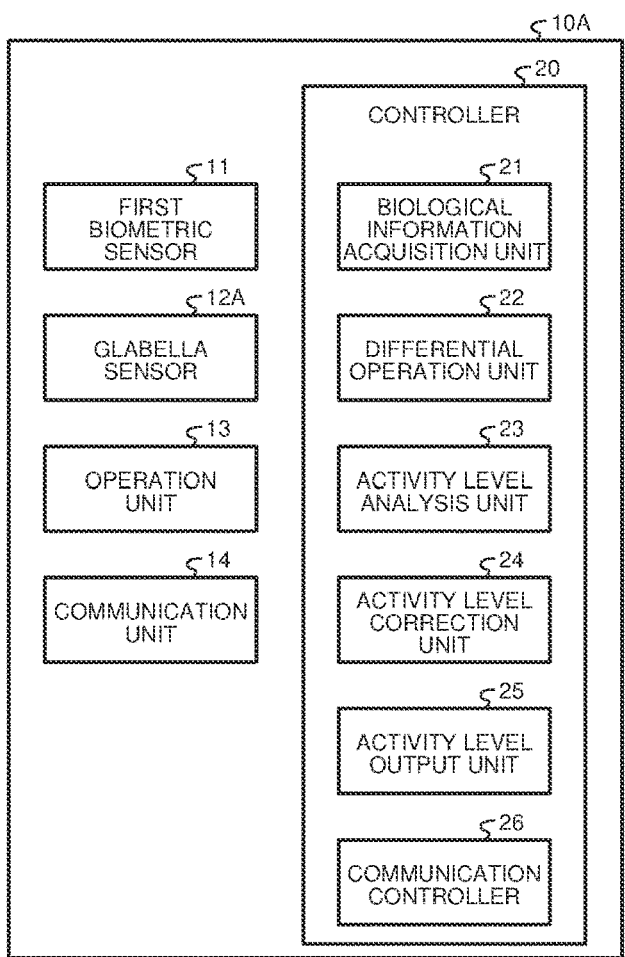
FIG. 7 is a block diagram illustrating a configuration example of a measurement apparatus according to a second embodiment.

A measurement apparatus according to a second embodiment will be described below with reference to FIG. 7. FIG. 7 is a block diagram illustrating a configuration example of the measurement apparatus according to the second embodiment.

Figure 8:
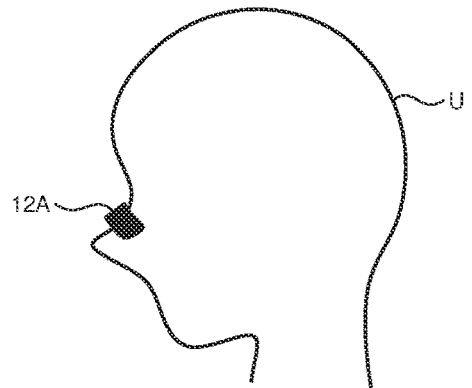
FIG. 8 is a diagram for explaining a mounting position of a glabella sensor.

As illustrated in FIG. 7, a measurement apparatus 10A is different from the measurement apparatus 10 illustrated in FIG. 3 in that a glabella sensor 12A is provided instead of the second biometric sensor 12. The glabella sensor 12A is one example of a specific configuration of the second biometric sensor 12. FIG. 8 is a diagram for explaining a mounting position of the glabella sensor 12A. As illustrated in FIG. 8, the glabella sensor 12A is arranged in a portion of a glabella above a nose that comes into contact with a nose pad when a user U wears an eyeglasses-type wearable terminal for example, and determines a respiratory status of the user U. The glabella sensor 12A may be implemented by any of configurations as described below, for example.

The glabella sensor 12A may be implemented by, for example, a microphone that acquires sound. In this case, the glabella sensor 12A detects sound of a flow of air that passes through an inside of the nose of the user U. In general, a silent period that occurs when the flow of air stops at a time of change from "inspiration" to "expiration" is shorter than that from "expiration" to "inspiration". The glabella sensor 12A detects sound of "inspiration" and sound of "expiration" respectively. The glabella sensor 12A detects a timing at which the time interval is switched shortly as a change point at which the respiration is changed from "inspiration" to "expiration". The glabella sensor 12A measures the respiratory status based on the timing of the change point of the sound, and counts the change point of the sound as one respiration.

The glabella sensor 12A may be implemented by, for example, an air pressure sensor that detects air pressure. In this case, the glabella sensor 12A detects a change of air pressure inside the nose of the user U. As for the air pressure inside the nose, the air pressures is increased both in "expiration" and "inspiration". In general, a low-pressure period from decrease of the air pressure to increase of the air pressure at the time of change from "inspiration" to "expiration" is shorter than that from "expiration" to "inspiration". The glabella sensor 12A detects air pressure in "inspiration" and air pressure in "expiration" respectively. The glabella sensor 12A detects a timing at which the time interval is switched shortly as a change point at which the respiration is changed from "inspiration" to "expiration".

The glabella sensor 12A measures the respiratory status based on the timing of the change point of the air pressure, and counts the change point of the air pressure as one respiration.

The glabella sensor 12A may be implemented by, for example, a temperature sensor that detects temperature. As the temperature sensor, for example, a thermistor may be used. In this case, the glabella sensor 12A detects a change of temperature at a position of the nose pad on the user U. In general, pressure of a flow of air that passes through the inside of the nose in "inspiration" is higher than that in "expiration". Therefore, due to water evaporation in a nostril, a decrease of the temperature at the time of "inspiration" is slightly increased as compared to that at the time of "expiration". The glabella sensor 12A detects a temperature change in "inspiration" and a change in "expiration" respectively. The glabella sensor 12A detects a timing at which the temperature change is more increased as a change point at which the respiration is changed from "inspiration" to "expiration". The glabella sensor 12A measures the respiratory status based on the timing of the change point of the temperature, and counts the change point of the temperature as one respiration.

The glabella sensor 12A may be implemented by an infrared camera that is arranged so as to be oriented downward in the portion of the glabella, for example. In this case, the glabella sensor 12A detects a temperature change of air that may occur due to movement of airflow under the nose or at a tip of the mouth. In general, the temperature under the nose and at the tip of the mouth decreases in "inspiration" and increases in "expiration". That is, the glabella sensor 12A detects the change point at which the respiration is changed from "inspiration" to "expiration" based on whether the temperature under the nose or at the tip of the mouth has decreased or increased. The glabella sensor 12A measures the respiratory status based on the timing of the change point of the temperature and counts the change point of the temperature as one respiration.

As described above, in the second embodiment, the glabella sensor 12A that is arranged in the glabella of the user U or around the glabella is able to measure the respiratory status of the user U. Therefore, in the second embodiment, it is possible to correct the activity level of the autonomic nerve of the user U based on the respiratory status that is measured by the glabella sensor 12A.

Third Embodiment

Figure 9:
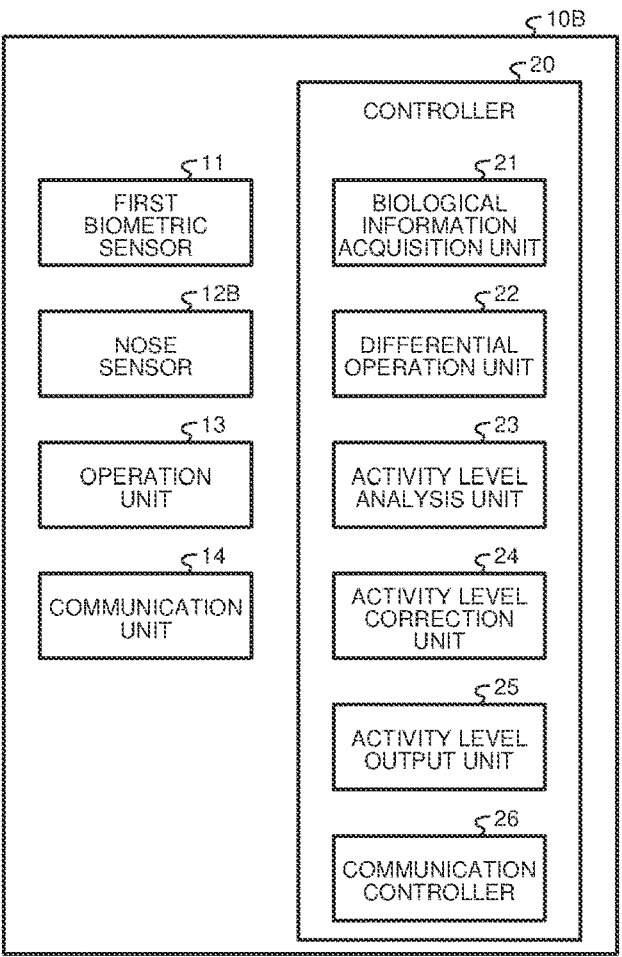
FIG. 9 is a block diagram illustrating a configuration example of a measurement apparatus according to a third embodiment.

A measurement apparatus according to the third embodiment will be described below with reference to FIG. 9. FIG. 9 is a block diagram illustrating a configuration example of the measurement apparatus according to the third embodiment.

Figure 10:
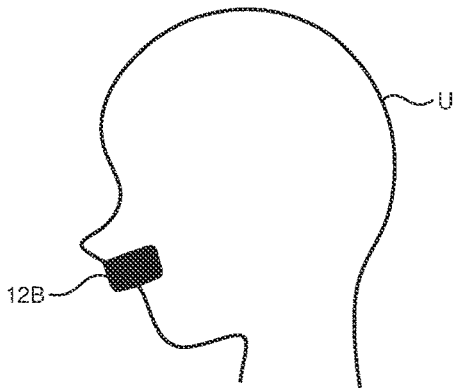
FIG. 10 is a diagram for explaining a mounting position of a nose sensor.

As illustrated in FIG. 9, a measurement apparatus 10B is different from the measurement apparatus 10 illustrated in FIG. 3 in that a nose sensor 12B is provided instead of the second biometric sensor 12. The nose sensor 12B is one example of a specific configuration of the second biometric sensor 12. FIG. 10 is a diagram for explaining a mounting position of the nose sensor 12B. As illustrated in FIG. 10, the nose sensor 12B is arranged in a portion at an entrance to a nasal cavity when the user U wears an eyeglasses-type wearable terminal for example, and determines the respiratory status of the user U. The nose sensor 12B may be implemented by any of configurations as described below, for example.

The nose sensor 12B may be implemented by, for example, a microphone that acquires sound. In this case, the nose sensor 12B detects sound of a flow of air that passes through an inside of the nose of the user U. The nose sensor 12B detects sound of "inspiration" and sound of "expiration" respectively. The glabella sensor 12A detects a timing at which the time interval is switched shortly as a change point at which the respiration is changed from "inspiration" to "expiration". The glabella sensor 12A measures the respiratory status based on the timing of the change point of the sound, and counts the change point of the sound from "inspiration" to "expiration" as one respiration.

The nose sensor 12B may be implemented by, for example, an air pressure sensor that detects air pressure. In this case, the nose sensor 12B detects a change of air pressure inside the nose of the user U. The nose sensor 12B detects air pressure in "inspiration" and air pressure in "expiration" respectively. The glabella sensor 12A detects a timing at which the time interval is switched shortly as a change point at which the respiration is changed from "inspiration" to "expiration". The glabella sensor 12A measures the respiratory status based on the timing of the change point of the air pressure, and counts the change point of the air pressure from "inspiration" to "expiration" as one respiration.

The nose sensor 12B may be implemented by, for example, a temperature sensor that detects temperature. As the temperature sensor, for example, a thermistor may be used. In this case, the nose sensor 12B detects a change of temperature at a position of the nose pad on the user U. In general, pressure of a flow of air that passes through the inside of the nose in "inspiration" is higher than that in "expiration". Therefore, due to water evaporation in a nostril, a decrease of the temperature at the time of "inspiration" is slightly increased as compared to that at the time of "expiration". The nose sensor 12B detects a temperature change in "inspiration" and a change in "expiration" respectively. The nose sensor 12B detects a timing at which the temperature change is more increased as a change point at which the respiration is changed from "inspiration" to "expiration". The nose sensor 12B measures the respiratory status based on the timing of the change point of the temperature, and counts the change point of the temperature from "inspiration" to "expiration" as one respiration.

The nose sensor 12B may be implemented by an infrared camera that is arranged so as to be oriented toward the nostril in a portion of the nose, for example. In this case, the nose sensor 12B detects a temperature change of air that may occur due to movement of airflow inside the nose. In general, the temperature inside the nose decreases in "inspiration" and increases in "expiration". That is, the nose sensor 12B detects the change point at which the respiration is changed from "inspiration" to "expiration" based on whether the temperature inside the nose has decreased or increased. The nose sensor 12B measures the respiratory status based on the timing of the change point nose sensor 12B, and counts the change point of the temperature from "inspiration" to "expiration" as one respiration.

The nose sensor 12B may be implemented by, for example, a humidity sensor that is arranged in the portion of the nose. In this case, the nose sensor 12B detects a change of humidity in the nasal cavity. The humidity in the nasal cavity decreases during both of "expiration" and "inspiration" periods. In general, a high-humidity period from increase of the humidity to decrease of the humidity at the time of change from "inspiration" to "expiration" is shorter than that from "expiration" to "inspiration". The nose sensor 12B detects the humidity in "inspiration" and the humidity in "expiration" respectively. The nose sensor 12B detects a timing of change from high humidity to low humidity as a change point at which the respiration is changed from "inspiration" to "expiration". The nose sensor 12B measures the respiratory status based on the timing of the change point of the humidity, and counts the change point of the humidity from "inspiration" to "expiration" as one respiration.

The nose sensor 12B may be, for example, a carbon dioxide concentration sensor that is arranged in the portion of the nose. In this case, the nose sensor 12B measures a carbon dioxide concentration around the nose or around the tip of the mouth. In general, the carbon dioxide concentration decreases in the "inspiration" period and increases in the "expiration" period. The nose sensor 12B detects a change of the carbon dioxide concentration around the nose or around the tip of the mouth. The nose sensor 12B detects a timing of change from a low concentration to a high concentration as a timing of change from "inspiration" to "expiration". The nose sensor 12B measures the respiratory status based on the timing of the change point of the carbon dioxide concentration, and counts the change point of the carbon dioxide concentration from "inspiration" to "expiration" as one respiration.

As described above, in the third embodiment, the nose sensor 12B that is arranged at the entrance to the nasal cavity of the user U or around the entrance is able to measure the respiratory status of the user U. Therefore, in the third embodiment, it is possible to correct the activity level of the autonomic nerve of the user U based on the respiratory status that is measured by the nose sensor 12B.

Fourth Embodiment

Figure 11:
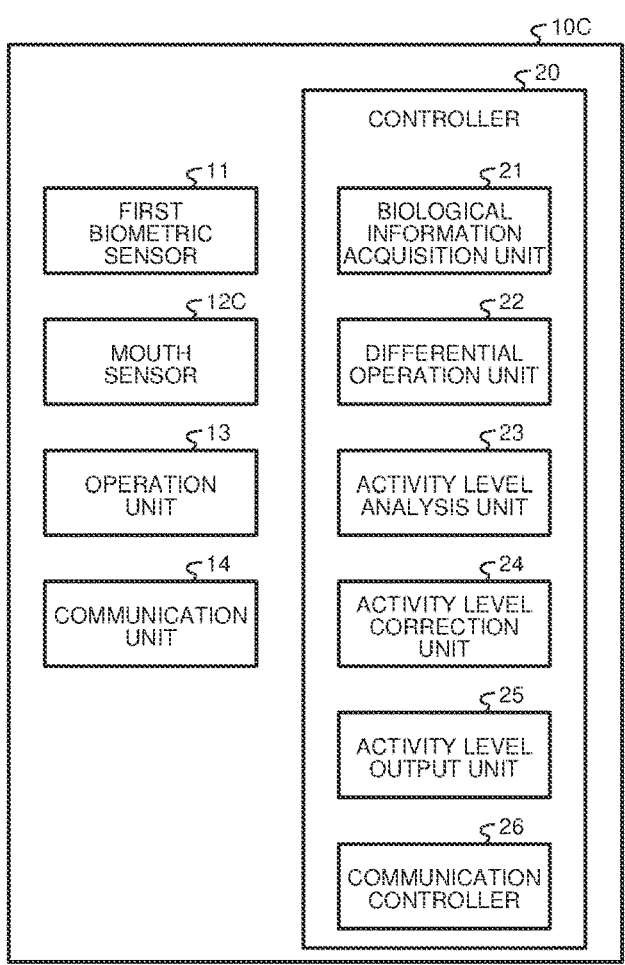
FIG. 11 is a block diagram illustrating a configuration example of a measurement apparatus according to a fourth embodiment.

A measurement apparatus according to a fourth embodiment will be described below with reference to FIG. 11. FIG. 11 is a block diagram illustrating a configuration example of the measurement apparatus according to the fourth embodiment.

Figure 12:
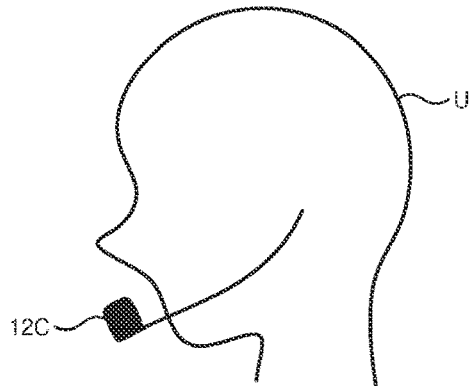
FIG. 12 is a diagram for explaining a mounting position of a mouth sensor.

As illustrated in FIG. 11, a measurement apparatus 10C is different from the measurement apparatus 10 illustrated in FIG. 3 in that a mouth sensor 12C is provided instead of the second biometric sensor 12. The mouth sensor 12C is one example of a specific configuration of the second biometric sensor 12. FIG. 12 is a diagram for explaining a mounting position of the mouth sensor 12C. As illustrated in FIG. 12, the mouth sensor 12C is arranged around the mouth when the user U wears a head-mounted wearable terminal for example, and determines the respiratory status of the user U. The mouth sensor 12C may be implemented by any of configurations as described below, for example.

The mouth sensor 12C may be implemented by, for example, a microphone that acquires voice. In this case, the mouth sensor 12C detects sound of a flow of air around the mouth of the user U. The mouth sensor 12C detects sound of "inspiration" and sound of "expiration" respectively. The mouth sensor 12C measures the respiratory status based on the timing of the change point of the sound, and counts the change point of the sound from "inspiration" to "expiration" as one respiration.

The mouth sensor 12C may be implemented by, for example, an air pressure sensor that detects air pressure. In this case, the mouth sensor 12C detects a change of air pressure inside the mouth of the user U. In general, a low-pressure period from decrease of the air pressure to increase of the air pressure at the time of change from "inspiration" to "expiration" inside the mouth is shorter than that from "expiration" to "inspiration". The mouth sensor 12C detects air pressure in "inspiration" and air pressure in "expiration" respectively. The mouth sensor 12C detects a timing at which the time interval is switched shortly as a change point at which the respiration is changed from "inspiration" to "expiration". The mouth sensor 12C measures the respiratory status based on the timing of the change point of the air pressure, and counts the change point of the air pressure from "inspiration" to "expiration" as one respiration.

The mouth sensor 12C may be implemented by, for example, a temperature sensor that detects temperature. As the temperature sensor, for example, a thermistor may be used. In this case, the mouth sensor 12C detects a change of temperature in an oral cavity of the user U. In general, pressure of a flow of air that passes inside the mouth in "inspiration" is higher than that in "expiration". Therefore, due to water evaporation in the oral cavity, a decrease of the temperature at the time of "inspiration" is slightly increased as compared to that at the time of "expiration". The mouth sensor 12C detects a temperature change in "inspiration" and a change in "expiration" respectively. The mouth sensor 12C detects a timing at which the temperature change is more increased as a change point at which the respiration is changed from "inspiration" to "expiration". The mouth sensor 12C measures the respiratory status based on the timing of the change point of the temperature, and counts the change point of the temperature from "inspiration" to "expiration" as one respiration.

The mouth sensor 12C may be implemented by an infrared camera that is arranged so as to be oriented toward a periphery of the mouth, for example. In this case, the mouth sensor 12C detects a temperature change of air that may occur due to movement of airflow around the mouth. In general, the temperature around the mouth decreases in "inspiration" and increases in "expiration". That is, the mouth sensor 12C detects the change point at which the respiration is changed from "inspiration" to "expiration" based on whether the temperature around the mouth has decreased or increased. The mouth sensor 12C measures the respiratory status based on the timing of the change point of the temperature, and counts the change point of the temperature from "inspiration" to "expiration" as one respiration.

The mouth sensor 12C may be implemented by, for example, a humidity sensor. In this case, the mouth sensor 12C detects a change of humidity in the oral cavity. The humidity in the nasal cavity decreases during both of "expiration" and "inspiration" periods. In general, a high-humidity period from increase of the humidity to decrease of the humidity at the time of change from "inspiration" to "expiration" is shorter than that from "expiration" to "inspiration". The mouth sensor 12C detects the humidity in "inspiration" and humidity in "expiration" respectively. The mouth sensor 12C detects a timing of change from high humidity to low humidity as a change point at which the respiration is changed from "inspiration" to "expiration". The nose sensor 12B measures the respiratory status based on the timing of the change point of the humidity and counts the change point of the humidity from "inspiration" to "expiration" as one respiration.

The mouth sensor 12C may be, for example, a carbon dioxide concentration sensor. In this case, the mouth sensor 12C measures carbon dioxide concentration around the nose or around the tip of the mouth. In general, the carbon dioxide concentration decreases in the "inspiration" period and increases in the "expiration" period. The mouth sensor 12C detects a change of the carbon dioxide concentration around the nose or around the tip of the mouth. The mouth sensor 12C detects a timing of change from a low concentration to a high concentration as a timing of change from "inspiration" to "expiration". The mouth sensor 12C measures the respiratory status based on the timing of the change point of the carbon dioxide concentration, and counts the change point of the carbon dioxide concentration from "inspiration" to "expiration" as one respiration.

As described above, in the fourth embodiment, the mouth sensor 12C that is arranged around the mouth of the user U is able to measure the respiratory status of the user U. Therefore, in the fourth embodiment, it is possible to correct the activity level of the autonomic nerve of the user U based on the respiratory status that is measured by the mouth sensor 12C.

Fifth Embodiment

Figure 13:
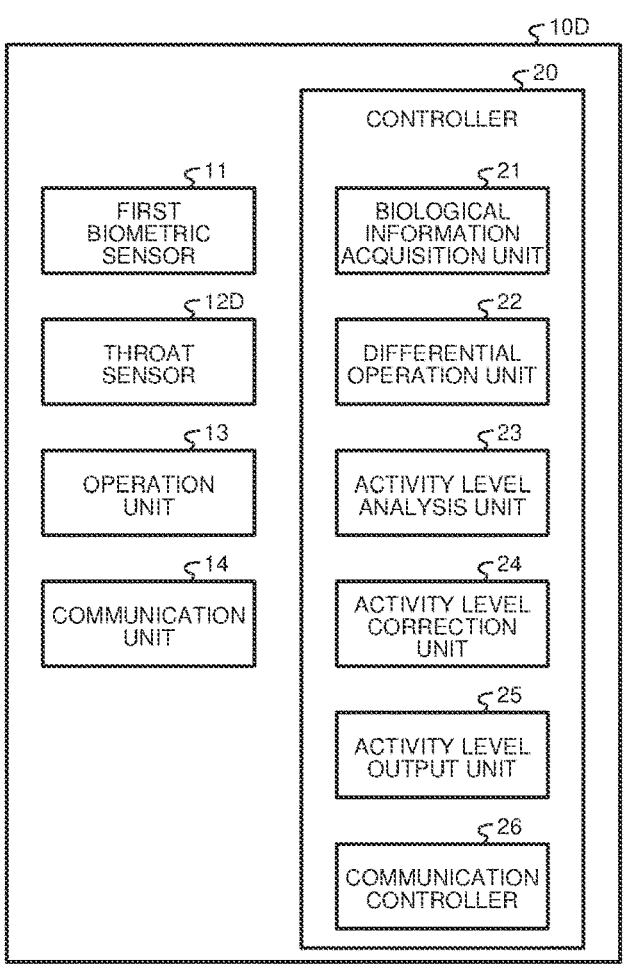
FIG. 13 is a block diagram illustrating a configuration example of a measurement apparatus according to a fifth embodiment.

A measurement apparatus according to a fifth embodiment will be described below with reference to FIG. 13. FIG. 13 is a block diagram illustrating a configuration example of the measurement apparatus according to the fifth embodiment.

Figure 14:
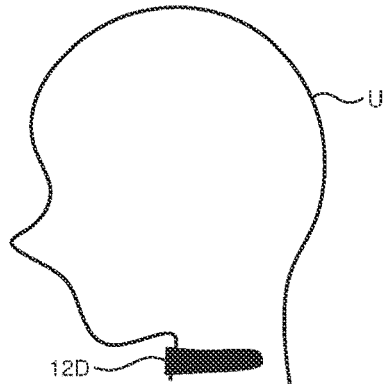
FIG. 14 is a diagram for explaining a mounting position of a throat sensor.

As illustrated in FIG. 13, a measurement apparatus 10D is different from the measurement apparatus 10 illustrated in FIG. 3 in that a throat sensor 12D is provided instead of the second biometric sensor 12. The throat sensor 12D is one example of a specific configuration of the second biometric sensor 12. FIG. 14 is a diagram for explaining a mounting position of the throat sensor 12D. As illustrated in FIG. 14, the throat sensor 12D is arranged around a throat when the user U wears a head-mounted wearable terminal for example, and determines the respiratory status of the user U. The throat sensor 12D may be implemented by any of configurations as described below, for example.

The throat sensor 12D may be implemented by, for example, a microphone that acquires voice. In this case, the throat sensor 12D detects sound of a flow of air around the mouth of the user U. The throat sensor 12D detects sound of "inspiration" and sound of "expiration" respectively. The throat sensor 12D measures the respiratory status based on the timing of the change point of the sound, and counts the change point of the sound from "inspiration" to "expiration" as one respiration.

The throat sensor 12D may be implemented by, for example, a temperature sensor that detects temperature. As the temperature sensor, for example, a thermistor may be used. In this case, the throat sensor 12D detects a change of temperature in the oral cavity at a position of the throat of the user U. The throat sensor 12D detects a temperature change in "inspiration" and a change in "expiration" respectively. The throat sensor 12D detects a timing at which the temperature change is more increased as a change point at which the respiration is changed from "inspiration" to "expiration". The throat sensor 12D measures the respiratory status based on the timing of the change point of the temperature, and counts the change point of the temperature from "inspiration" to "expiration" as one respiration.

The throat sensor 12D may be implemented by an infrared camera that is arranged so as to be oriented toward a periphery of the mouth, for example. In this case, the throat sensor 12D detects a temperature change of air that may occur due to movement of airflow around the mouth. The throat sensor 12D detects the change point at which the respiration is changed from "inspiration" to "expiration" based on whether the temperature around the mouth has decreased or increased. The throat sensor 12D measures the respiratory status based on the timing of the change point of the temperature, and counts the change point of the temperature from "inspiration" to "expiration" as one respiration.

The throat sensor 12D may be, for example, a carbon dioxide concentration sensor. In this case, the throat sensor 12D measures carbon dioxide concentration around the mouth. The throat sensor 12D detects a change of the carbon dioxide concentration around the mouth. The throat sensor 12D detects a timing of change from a low concentration to a high concentration as a timing of change from "inspiration" to "expiration". The throat sensor 12D measures the respiratory status based on the timing of the change point of the carbon dioxide concentration, and counts the change point of the carbon dioxide concentration from "inspiration" to "expiration" as one respiration.

As described above, in the fifth embodiment, the throat sensor 12D that is arranged around the throat of the user U is able to measure the respiratory status of the user U. Therefore, in the fifth embodiment, it is possible to correct the activity level of the autonomic nerve of the user U based on the respiratory status that is measured by the throat sensor 12D.

Sixth Embodiment

Figure 15:
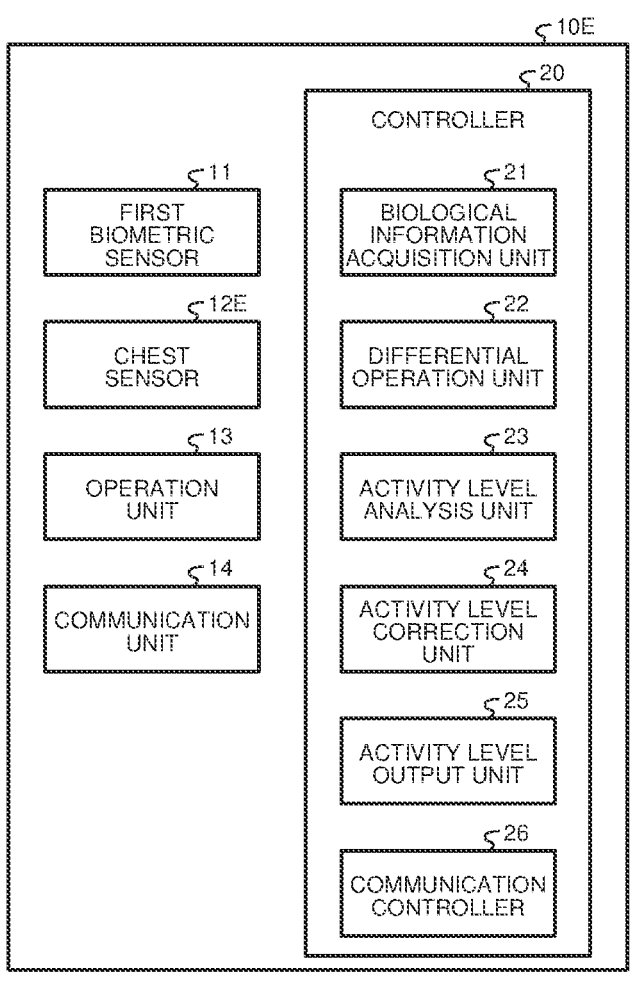
FIG. 15 is a block diagram illustrating a configuration example of a measurement apparatus according to a sixth embodiment.

A measurement apparatus according to a sixth embodiment will be described below with reference to FIG. 15. FIG. 15 is a block diagram illustrating a configuration example of the measurement apparatus according to the sixth embodiment.

Figure 16A:
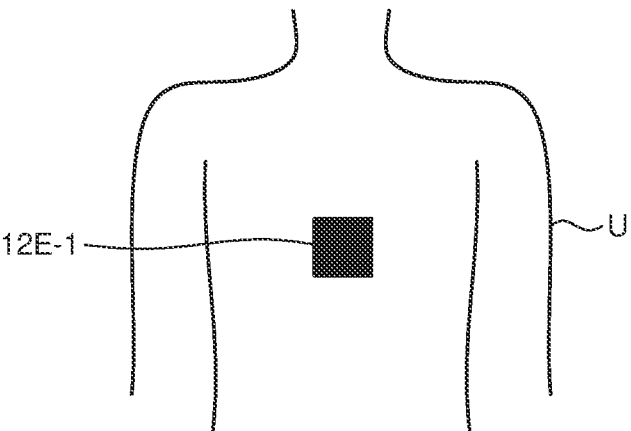
FIG. 16A is a diagram for explaining a mounting position of a chest sensor.
Figure 16B:
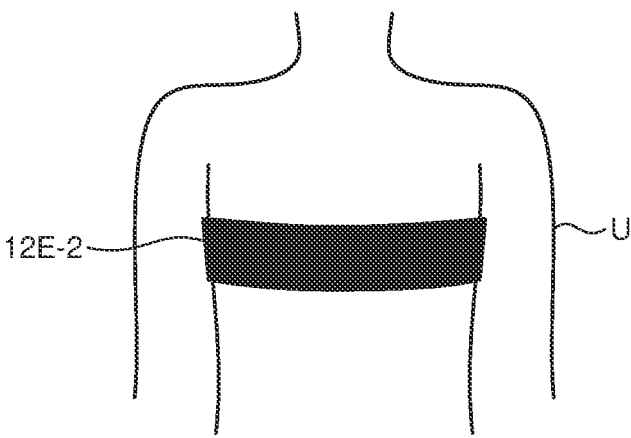
FIG. 16B is a diagram for explaining a mounting position of a chest sensor.
Figure 16C:
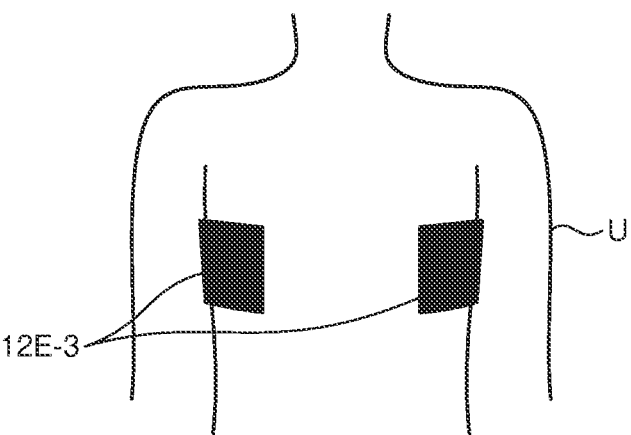
FIG. 16C is a diagram for explaining a mounting position of a chest sensor.

As illustrated in FIG. 15, a measurement apparatus 10E is different from the measurement apparatus 10 illustrated in FIG. 3 in that a chest sensor 12E is provided instead of the second biometric sensor 12. The chest sensor 12E is one example of a specific configuration of the second biometric sensor 12. FIG. 16A, FIG. 16B, and FIG. 16C are diagrams for explaining mounting positions of the chest sensor 12E. FIG. 16A is a diagram for explaining a first example of the sixth embodiment. As illustrated in FIG. 16A, a chest sensor 12E-1 is worn on a portion in the vicinity of a chest portion that is located near the heart of the user U. FIG. 16B is a diagram for explaining a second example of the sixth embodiment. As illustrated in FIG. 16B, a chest sensor 12E-2 is worn so as to be wound around the chest portion of the user U once. FIG. 16C is a diagram for explaining a third example of the sixth embodiment. As illustrated in FIG. 16C, chest sensors 12E-3 are worn on certain muscles on both sides of the chest of the user U. The chest sensor 12E-1 to the chest sensor 12E-3 may be collectively referred to as the chest sensor 12E when they need not be distinguished from one another. As illustrated in FIG. 16A to FIG. 16C, the chest sensor 12E is a wearable terminal that is worn on the body, for example.

First, the chest sensor 12E-1 illustrated in FIG. 16A will be described.

The chest sensor 12E-1 may be implemented by, for example, a microphone that acquires sound. In this case, the chest sensor 12E-1 detects sound of a flow of air that passes through lungs of the user U. The chest sensor 12E-1 detects sound of "inspiration" and sound of "expiration" respectively. The chest sensor 12E-1 measures the respiratory status based on the timing of the change point of the sound, and counts the change point of the sound from "inspiration" to "expiration" as one respiration.

The chest sensor 12E-1 may be configured to detect a change in a perimeter length of the trunk of the user U, for example. In this case, a period in which the perimeter length of the trunk is increased corresponds to the "inspiration" period, and the period in which the perimeter length of the trunk is reduced corresponds to the "expiration" period. In general, a period in which the increase and the decrease of the perimeter length of the trunk are stopped at the time of change from "inspiration" to "expiration" is shorter than that from "expiration" to "inspiration". The chest sensor 12E-1 measures the respiratory status based on the timing at which the increase and the decrease of the perimeter length of the trunk of the body are switched, and counts a change point from "inspiration" to "expiration" as one respiration.

The chest sensor 12E-2 illustrated in FIG. 16B will be described below.

The chest sensor 12E-2 is wound around the body portion of the user U and configured to measure a change of tension that may occur with a change in the perimeter length of the trunk. The chest sensor 12E-2 is configured by using, for example, a stretchable variable resistance element in which an electrical resistance value changes due to stretch. In this case, a period in which the tension is increased corresponds to the "inspiration" period and a period in which the tension is reduced corresponds to the "expiration" period. In general, a period in which the increase and the decrease of the tension are stopped at the time of change from "inspiration" to "expiration" is shorter than that from "expiration" to "inspiration". The chest sensor 12E-2 measures the respiratory status based on the timing of a change point at which the increase and the decrease of the tension are switched, and counts the change point from "inspiration" to "expiration" as one respiration.

The chest sensor 12E-3 illustrated in FIG. 16C will be described below.

The chest sensor 12E-3 is configured with, for example, a myoelectric potential sensor that measures myopotential of a muscle of the chest. In this case, the chest sensor 12E-3 is configured to measure a weak electrical signal that is generated in accordance with contraction of the muscle by electrodes. The muscle to be measured is what is called a respiratory muscle. Examples of the respiratory muscle include a diaphragm, an internal intercostal muscle, an external intercostal muscle, a sternocleidomastoid muscle, an anterior scalene muscle, a middle scalene muscle, a posterior scalene muscle, a rectus abdominal muscle, an internal abdominal oblique muscle, an external abdominal oblique muscle, and a transverse abdominal muscle. The myoelectric potential is generated when the muscle contracts. Among the respiratory muscles, the diaphragm and the external intercostal muscle are largely contracted at a time of "inspiration", as compared to the other respiratory muscles. Therefore, in the present embodiment, it is preferable to measure myoelectric potential of the thoracic diaphragm and the external intercostal muscle in which a degrees of contraction is large. In FIG. 16C, the chest sensors 12E-3 are worn near underarms of the user U, but practically, the chest sensors 12E-3 are worn on a position where the respiratory muscles as measurement targets are present. Specifically, two electrodes of the chest sensors 12E-3 are attached along portions of muscle fibers for which the myopotential is to be measured, and an electrical signal between the electrodes is measured for measuring the myoelectric potential. In this case, a period in which a larger myoelectric potential is generated corresponds to the "inspiration" period and a period in which a weak or no myoelectric potential is generated corresponds to the "inspiration"

period. In general, a timing at which the myoelectric potential drops is a timing of change from "inspiration" to "expiration". The chest sensor 12E-3 measures the respiratory status based on the timing of a change point at which the magnitude of the myopotential is switched, and counts the change point from "inspiration" to "expiration" as one respiration.

As described above, in the sixth embodiment, the chest sensor 12E that is worn on the body of the user U is able to measure the respiratory status of the user U. Therefore, in the sixth embodiment, it is possible to correct the activity level of the autonomic nerve of the user U based on the respiratory status that is measured by the chest sensor 12E.

Thus, the embodiments of the present application have been described above, but the present application is not limited by the details of the embodiments. Further, the components described above include one that can easily be thought of by a person skilled in the art, one that is practically identical, and one that is within an equivalent range. Furthermore, the components described above may be combined appropriately. Moreover, within the scope not departing from the gist of the embodiments described above, various omission, replacement, and modifications of the components may be made.

For example, in the embodiments of the present application, it may be possible to use electrocardiogram information, which is caused by a biological mechanism that generates a pulse, measurement information, which is obtained by measuring motion of the hear by using sound waves or electromagnetic waves, and the like, instead of the information on the R-R wave interval using a pulse wave. Further, as the method of measuring the respiratory status, it may be possible to use motion of a living body, a flow of air, and a change of body temperature linked therewith as long as it is possible to determine a difference between expiration and inspiration.

INDUSTRIAL APPLICABILITY

The measurement apparatus, the measurement method, and the program of the present embodiments may be used for, for example, medical apparatuses.

According to the present application, it is possible to appropriately correct an error that is included in a measurement result of an activity level of an autonomic nerve.

Although the application has been described with respect to specific embodiments for a complete and clear application, the appended claims are not to be thus limited but are to be construed as embodying all modifications and alternative constructions that may occur to one skilled in the art that fairly fall within the basic teaching herein set forth.

What is claimed is:
1. A measurement apparatus comprising:
   a first biometric sensor configured to measure, as a biological signal, at least one of a brain wave signal and a pulse wave signal of a living body;
   a second biometric sensor configured to measure a respiratory rate of the living body per unit time;
   a memory that is configured to store computer executable instructions; and
   at least one processor that is configured to execute the computer executable instructions to perform operations, comprising:
      calculating a differential value of a periodic feature of the biological signal;

analyzing an activity level of an autonomic nerve of the living body based on the differential value of the periodic feature of the biological signal; and correcting the activity level of the autonomic nerve of the living body by eliminating a component that is caused by respiration of the living body and that is included in the activity level of the autonomic nerve of the living body, based on the respiratory rate of the living body per unit time, wherein the correcting further comprises correcting the activity level of the autonomic nerve of the living body by using the respiratory rate of the living body per unit time and a respiratory rate in a steady state.

2. The measurement apparatus according to claim 1, wherein the correcting further comprises correcting the activity level of the autonomic nerve of the living body by using a ratio of the respiratory rate of the living body per unit time to a respiratory rate in a steady state.

3. The measurement apparatus according to claim 1, wherein the second biometric sensor is a sensor that is mounted on one of a glabella portion, a nose, a mouth, a throat, and a chest of the living body.

4. A measurement method of a measurement apparatus comprising a first biometric sensor, a second biometric sensor, a memory, and at least one processor configured to execute processes, the processes comprising:

measuring, as a biological signal by the first biometric sensor, at least one of a brain wave signal and a pulse wave signal of a living body;

measuring, by the second biometric sensor, a respiratory rate of the living body per unit time;

calculating a differential value of a periodic feature of the biological signal;

analyzing an activity level of an autonomic nerve of the living body based on the differential value of the periodic feature of the biological signal; and correcting the activity level of the autonomic nerve of the living body by eliminating a component that is caused by respiration of the living body and that is included in the activity level of the autonomic nerve of the living body based on the respiratory rate of the living body per unit time, wherein the correcting further comprises correcting the activity level of the autonomic nerve of the living body by using the respiratory rate of the living body per unit time and a respiratory rate in a steady state.

5. A non-transitory storage medium that stores a program for a measurement apparatus comprising a first biometric sensor, a second biometric sensor, a memory, and at least one processor, the program, when executed by the at least one processor, facilitates performance of operations comprising:

measuring, as a biological signal, at least one of a brain wave signal and a pulse wave signal of a living body;

measuring a respiratory rate of the living body per unit time;

calculating a differential value of a periodic feature of the biological signal;

analyzing an activity level of an autonomic nerve of the living body based on the differential value of the periodic feature of the biological signal; and correcting the activity level of the autonomic nerve of the living body by eliminating a component that is caused by respiration of the living body and that is included in the activity level of the autonomic nerve of the living body based on the respiratory rate of the living body per unit time, wherein the correcting further comprises correcting the activity level of the autonomic nerve of the living body by using the respiratory rate of the living body per unit time and a respiratory rate in a steady state.

* * * * *